US 6,570,651 B1

(12) United States Patent
Haubold et al.

(10) Patent No.: US 6,570,651 B1
(45) Date of Patent: May 27, 2003

(54) METHOD AND DEVICE FOR DETECTING FAULTS IN FLAT GLASS, ESPECIALLY DRIPS, THREADS AND LINES

(75) Inventors: Wolfgang Haubold, Bielefeld (DE); Josef Droste, Glandorf (DE); Edmund Paneff, Bielefeld (DE)

(73) Assignee: Lasor AG (DE)

( * ) Notice: Subject to any disclaimer, the term of this patent is extended or adjusted under 35 U.S.C. 154(b) by 0 days.

(21) Appl. No.: 09/646,861

(22) PCT Filed: Mar. 24, 1999

(86) PCT No.: PCT/EP99/02244

§ 371 (c)(1),
(2), (4) Date: Sep. 25, 2000

(87) PCT Pub. No.: WO99/49304

PCT Pub. Date: Sep. 30, 1999

(30) Foreign Application Priority Data

Mar. 25, 1998 (DE) .......................... 198 13 073

(51) Int. Cl.$^7$ ................................................ G01N 21/88
(52) U.S. Cl. ................................ 356/239.1; 356/237.1; 356/430
(58) Field of Search ........................... 356/239.1–239.8, 356/237.1–237.5, 430; 65/29.12; 250/559.46

(56) References Cited

U.S. PATENT DOCUMENTS

| 4,570,074 A | * | 2/1986 | Jette ........................ 250/559.49 |
| 5,452,079 A | * | 9/1995 | Okugawa ................... 356/239.1 |
| 5,691,811 A | * | 11/1997 | Kihira ....................... 356/239.1 |

* cited by examiner

*Primary Examiner*—Richard A. Rosenberger
*Assistant Examiner*—Vincent P. Barth
(74) *Attorney, Agent, or Firm*—Diller, Ramik & Wight

(57) ABSTRACT

The invention relates to a method of determining the optical quality of and detecting faults in flat glass (2) and other transparent materials, especially in float glass, wherein a video camera (1) is arranged to monitor an illuminating device (3) either through the glass (2) or by observing the reflection thereof, the focus being on the glass (2) and the sheet, respectively, and the video camera (1) generates signals in dependence on the quality of the glass (2) and these signals are evaluated, wherein use is made of at least one illuminating device (3), comprising a pattern (4) of adjacent partial portions (5a,5b) alternately different at least in color and/or in intensity, an observation spot of the video camera (1) picks up the pattern (4), two video signals $U_1, U_2$ are assigned to the signal of the pattern (4), and a change of the intensity of the video signals U1,U2 is used for evaluating the quality of the glass (2) and the sheet, respectively.

10 Claims, 3 Drawing Sheets

FIG.2
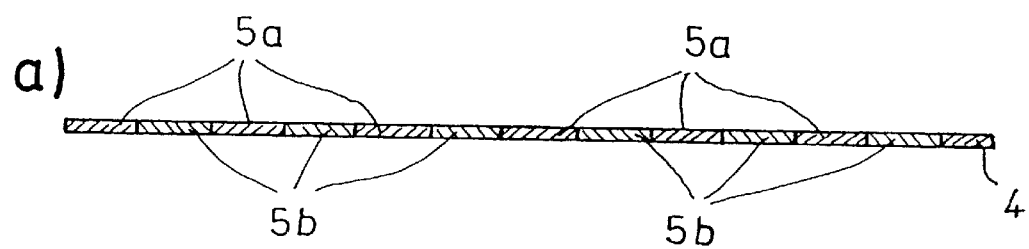
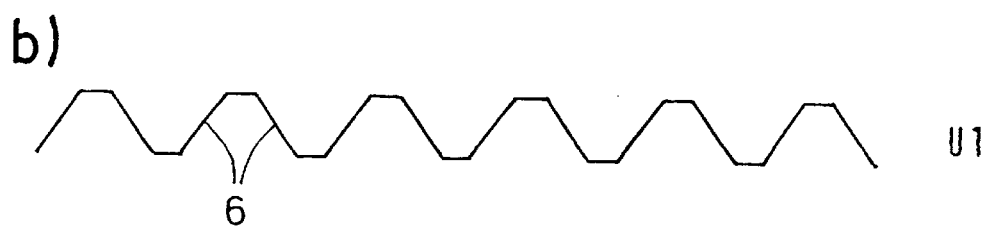
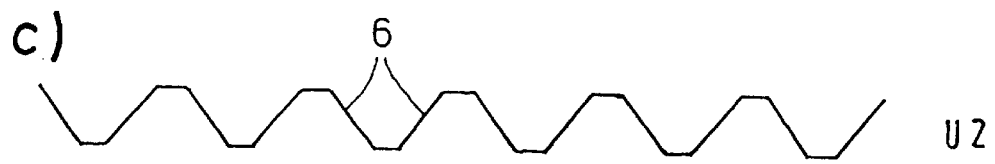

METHOD AND DEVICE FOR DETECTING FAULTS IN FLAT GLASS, ESPECIALLY DRIPS, THREADS AND LINES

The invention relates to a method of determining the optical quality of and for detecting faults in flat glass.

BACKGROUND OF THE INVENTION

A method is known for determining the optical quality of flat glass, especially of float glass, where in a video camera is arranged to monitor illumination through glass or a transparent sheet. In the process, the video camera receives signals according to the quality of the glass. These signals will subsequently be evaluated.

In the production of glass or other transparent materials, it may happen that lines in the longitudinal direction and threads and faults with slight optical deformation are generated which have an optical deflection only in the transverse direction of the sheet. Such faults cannot be detected by conventional dark-field techniques and other methods which pick up the deflection in the longitudinal direction only.

SUMMARY OF THE INVENTION

In the following, a novel method of detecting glass faults will be presented. The method detect's the deflection of a glass fault in the transverse direction of the glass sheet and is particularly suited for the detection of lines, threads and faults with slight optical deformation (drips).

The inventive method is characterized in that at least one illuminating device comprising a pattern of adjacent partial portions alternately different at least in color and/or in intensity is used, an observation spot of the video camera picks up the pattern, two video signals $U_1, U_2$ are assigned to the signal of the pattern, and a change of the intensity of the video signals $U_1, U_2$ is used for evaluating the quality of the glass and the sheet, respectively.

According to an advantageous embodiment of the invention, use is made of a two-colored pattern comprising partial portions of alternating colors, and the video camera includes a color chip, with the video signals assigned respectively to one color.

Suitably, the width of the partial portions is slightly larger or smaller than the lateral length of the observation spot. Only the evaluation is changed in the given case.

In an alternative advantageous embodiment of the invention, the pattern comprises partial portions of alternating bright and dark zones. Advantageously, the partial portions are illuminated and obscured cyclically in predetermined phases.

Suitably, a second, identical illuminating device is used whose pattern is arranged at a displacement by half of the width of a partial portion relative to the pattern of the first illuminating device. In this manner, dead zones are excluded.

Advantageously, the difference between the two video signals $U_1, U_2$ is used as a measure of the deflection caused by the fault in the glass.

According to a particular embodiment, the relation $$Upos = \frac{U_1 - U_2}{U_1 + U_2}$$

is used as a measure of the deflection caused by the fault.

Advantageously, for measuring the core of the fault in the glass, use is made of a deviation from the maximum value of the addition of $U_1$ and $U_2$, i.e. from $U_h = U_1 + U_2$.

BRIEF DESCRIPTION OF THE DRAWINGS

Further embodiments of the invention are evident from the Figures which will be described hereunder.

FIG. 2 is a diagrammatic view, and illustrates a representation of the two video signals $U_1, U_2$ according to FIG. 1.

DESCRIPTION OF THE PREFERRED EMBODIMENT

Figure 1:
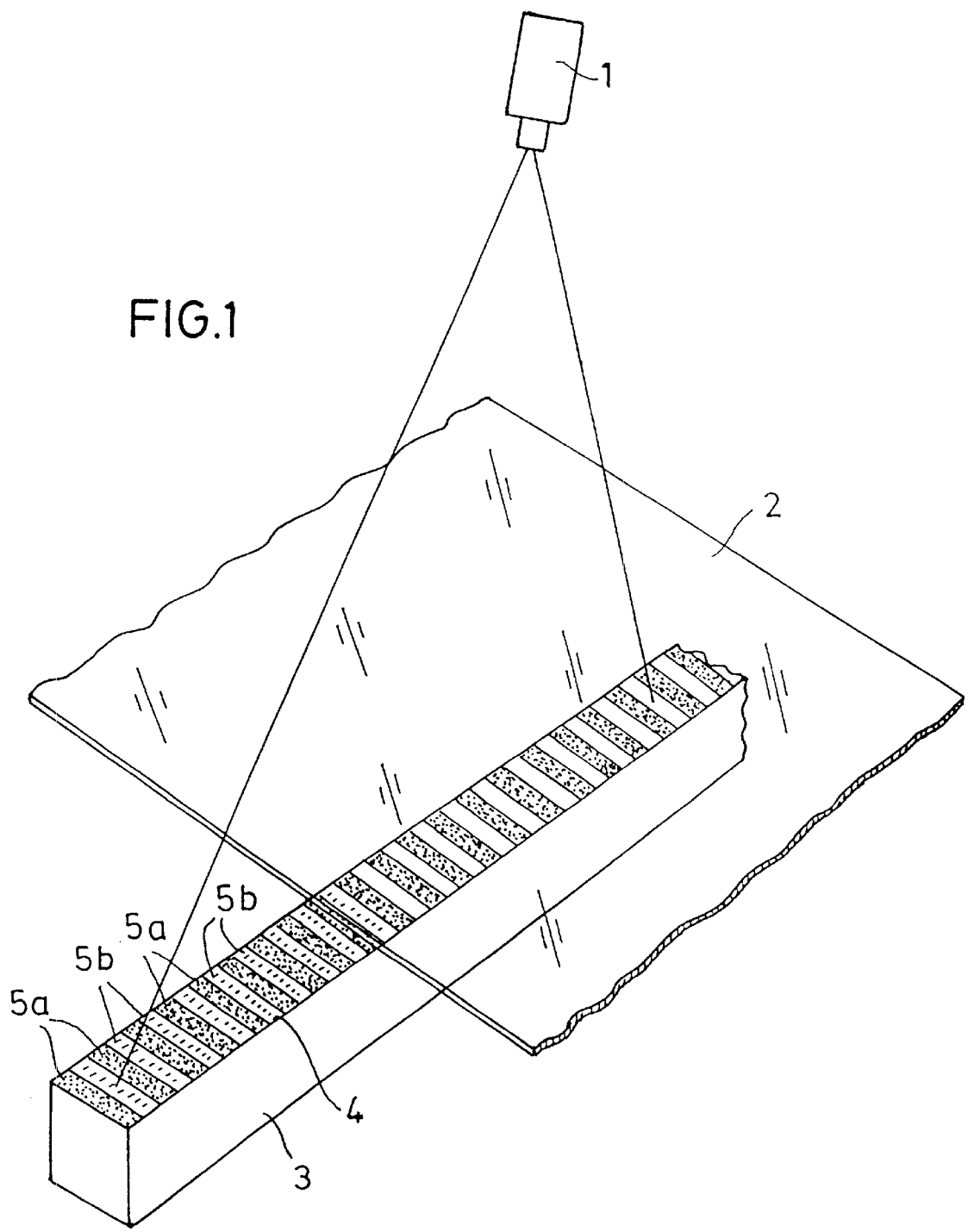
FIG. 1 is a fragmentary schematic perspective view, and; illustrates the inventive method performed by use of a two-colored pattern.

FIG. 1 shows a schematic illustration of the inventive method. The line camera 1, provided as a color camera, views the illuminating device 3 through the glass 2 by observing the reflection of the illumination. The focus of the camera 1 is on the plane of the glass 2. According to the depth of focus, the viewing rectangle has a lateral length on the illuminating device in a range from a few millimeters to several centimeters, depending on the respective setting of the aperture. The illuminating device has a pattern 4 applied thereon comprising two different colors (e.g. red, green) in alternate arrangement. The color bars or partial portions 5a, 5b have a width slightly larger or smaller than the lateral length of the viewing rectangle. Thus, the video signals $U_1, U_2$ generated by the camera 1 are a result of bright/dark jumps displaced by 180°, with a respective shape of an equal-sided trapeze (FIG. 2).

The two legs 6 of the trapeze are the zones in which the detection of deflections resulting from optical deformation is performed. Such deflections are generated on a site where the field of view of the camera 1 extends beyond the border of two zones 5a, 5b. In such a viewing field, video signals with opposite voltage developments are generated. In the region of the legs 6 of the trapeze, application of $$Upos = \frac{U_1 - U_2}{U_1 + U_2}$$

results in a video signal $U_1, U_2$ having a voltage development which is dependent on the position of the viewing rectangle. Optical deformations which cause the viewing rectangle to be shifted in a direction transverse to the moving direction of the glass sheet 2, will disturb this voltage development. Through evaluation the current position-dependent voltage development, glass faults accompanied by deflections transverse to the direction of the sheet can be detected. Changes are a measure of the amount of the deflection. A disturbance by contamination influences both of the voltages and is eliminated in the above term.

By evaluation of a second pattern, displaced by 90°, the occurrence of dead zones is avoided.

Figure 3:
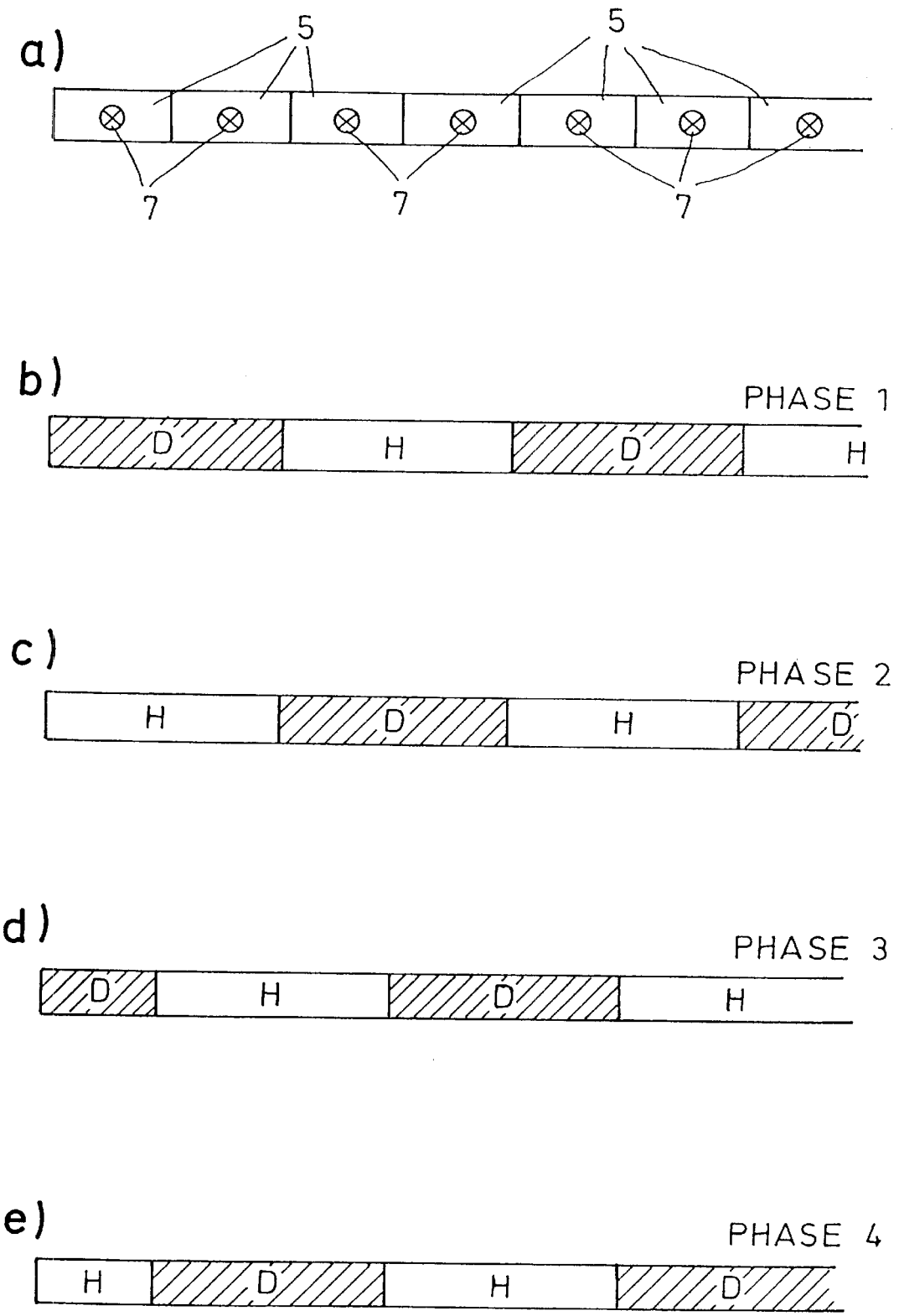
FIG. 3 is a schematical view, and illustrates the inventive method performed by use of an illuminating device comprising partial portions of alternating bright and dark zones.

This evaluation can also be carried out by means of BW cameras while choosing the illumination color at random. In this case, the illuminating device is divided into smaller segments 5. The video signals $U_1$ and $U_2$ are generated in that the illumination by the lamps 7 is switched from scan to scan. $U_1$ and $U_2$ are generated in the phases 1 and 2 and, displaced by 90°, in the phases $U_3$ and $U_4$. This switching is performed cyclically (FIG. 3).

Although a preferred embodiment of the invention has been specifically illustrated and described herein, it is to be understood that minor variations may be made in the apparatus without departing from the spirit and scope of the invention, as defined the appended claims.

We claim:

1. A method of determining the optical quality of and detecting faults in transparent material (2) wherein a video camera (1) is arranged to monitor the emitted light of an illuminating device (3) that either is transmitted through or is reflected by the transparent material (2), the focus being on the transparent material (2), and the video camera (1) generates signals in dependence on the quality of the transparent material (2) and these signals are evaluated, characterized by using at least one illuminating device (3) for creating a pattern (4) of adjacent partial portions (5a, 5b) alternately different at least in color and/or in intensity, picking up the pattern (4) in a field of view of the video camera (1), generating a first video signal $U_1$ caused by the light transmitted through a first partial portion (5a, 5b) of the pattern (4) and generating a second video signal $U_2$ caused by light transmitted through the second partial pattern (5b, 5a) of the pattern (4), and evaluating the quality of the transparent material (2) by utilizing a change of the intensity of the video signals $U_1$, $U_2$.

2. The method according to claim 1, characterized in that the use is made of a two-colored pattern (4) wherein the partial portions (5a, 5b) are of alternating colors, the video camera (1) includes a color chip, and the video signals $U_1$, $U_2$ are assigned respectively to one color.

3. The method according to claim 1, characterized in that the width of the lateral length of the field of view is smaller than twice the width of the partial portions (5a, 5b).

4. The method according to claim 1, characterized in that the partial portions (5a, 5b) are alternating bright and dark zones.

5. The method according to claim 4, characterized in that the partial portions (5a,5b) are illuminated and obscured cyclically in predetermined phases.

6. The method according to claim 1, characterized in that a second, identical illuminating device (3) is used whose pattern (4) is arranged at a displacement by half of the width of a partial portion (5a,5b) relative to the pattern (4) of the first illuminating device (3).

7. The method according to claim 1, characterized in that the difference between the two video signals $U_1$ and $U_2$ is used as a measure of the deflection caused by the fault in the transparent material (2).

8. The method according to claim 7, characterized in that the relation $$Upos = \frac{U_1 - U_2}{U_1 + U_2}$$

is used as a measure of the deflection caused to the fault.

9. The method according to claim 1, characterized in that for measuring the core of the fault in the transparent material (2), use is made of a deviation from the maximum value of the addition of $U_1$ and $U_2$, i.e. from $U_h = U_1 + U_2$.

10. The method according to claim 2, characterized in that the width of the lateral length of the field of view is smaller than twice the width of the partial portions (5a, 5b).

* * * * *